(12) United States Patent
Toor (10) Patent No.: US 8,091,567 B2
(45) Date of Patent: Jan. 10, 2012

(54) CUSTOM INSTANT FLOSSING APPLIANCE

(76) Inventor: Viranmol Toor, Ontario (CA)

( * ) Notice: Subject to any disclaimer, the term of this patent is extended or adjusted under 35 U.S.C. 154(b) by 429 days.

(21) Appl. No.: 12/364,029

(22) Filed: Feb. 2, 2009

(65) Prior Publication Data

US 2009/0194133 A1    Aug. 6, 2009

(30) Foreign Application Priority Data

Feb. 4, 2008    (CA) ..................................... 2619089

(51) Int. Cl.
*A61C 15/00*    (2006.01)
(52) U.S. Cl. ......................................................... 132/324
(58) Field of Classification Search ........... 132/323–329; 433/6
See application file for complete search history.

(56) References Cited

U.S. PATENT DOCUMENTS

| | | | |
|---|---|---|---|
| 5,022,417 A * | 6/1991 | Cimini | ........................... 132/323 |
| 5,429,145 A | 7/1995 | Bral | |
| 5,613,508 A | 3/1997 | Bushman | |
| 6,926,027 B1 * | 8/2005 | Sorensen | .................. 137/355.12 |
| 2006/0014121 A1 * | 1/2006 | DelGrosso | ..................... 433/216 |

* cited by examiner

*Primary Examiner* — Rachel Steitz (74) *Attorney, Agent, or Firm* — Notaro, Michalos & Zaccaria P.C.

(57) ABSTRACT

A custom-designed oral appliance for simultaneously flossing all the user's teeth. Consists of a custom-fitted polymer mouthpiece containing two corresponding holes located at the gum line between adjacent teeth, where one hole is located on the lingual side and one hole is located on the buccal side of the apparatus. Typical floss is then threaded through the appliance such that it matches the individual user's tooth pattern. New floss can be dispensed through the appliance and spent floss collected by means of a floss distribution system. A further embodiment provides a cross flossing pattern to maximize floss contact with the inter-proximal surfaces of adjacent teeth.

13 Claims, 6 Drawing Sheets

CUSTOM INSTANT FLOSSING APPLIANCE

FIELD OF THE INVENTION

The present invention relates to a custom instant flossing appliance. Specifically, the present appliance is custom fitted to the individual user such that floss can be threaded thorough provided holes in the pattern of the user's teeth. Further embodiments can have floss distribution systems whereby new floss is distributed and used floss is collected by means of dispensing and collecting reels accordingly. Another embodiment consists of an improved appliance, wherein two strands of floss are passed through the inter-proximal areas of the user's adjacent teeth in an x-shaped pattern, such that each strand of floss maintains better contact with the inter-proximal tooth surface, providing improved cleaning.

BACKGROUND OF THE INVENTION

It is universally accepted by dental professionals that regular flossing is an integral part of a successful oral hygiene regimen. Flossing in the inter-proximal spaces of the teeth removes plaque which is responsible for both tooth decay and gum disease. However, regular flossing remains often neglected due to the time and effort it requires. Many users find that winding the floss around the fingers can be painful.

The present invention aims to reduce the inconvenience and time required to floss by providing an appliance that can simultaneously floss all the teeth at once. Furthermore, new floss can be easily advanced through the appliance via a distribution system when the floss has outlived it's usefulness. An improved version of the invention provides a cross-flossing arrangement whereby the floss maintains better contact with the inter-proximal surfaces of adjacent teeth, providing an even more thorough cleaning.

Many different flossing appliances are known in the art. A popular flossing device is the flosser and dental pick. This device has a choice of two attachments (a power flosser, and a soft dental pick). This device is designed to reach between the teeth and below the gum line to remove plaque. However, this process is time consuming as each tooth must be cleaned separately.

Multi-tooth flossing devices are also known. Examples include U.S. Pat. No. 5,190,062 to Rafaeli and U.S. Patent Application No. 2006/0014121 A1 to DelGrosso. Both Rafaeli and DelGrosso disclose multi-tooth flossing devices which are custom fitted to the individual user's mouth. However, such devices have a number of drawbacks. For example, neither Rafaeli or DelGrosso provides a means for quickly advancing new floss through the appliance, forcing the user to undertake laborious re-threading of the appliance each time that new floss is required.

Furthermore, particularly effective cleaning is achieved when the floss maintains contact with as much of the inter-proximal surface of a tooth as possible. As can be appreciated, such surfaces are in fact curved, and therefore an arrangement whereby the floss can follow the contours of these surfaces will result in improved cleaning. Therefore, the present invention provides an embodiment whereby the two strands of floss pass through each inter-proximal area between adjacent teeth such that the floss experiences increased contact with the inter-proximal surfaces of the teeth being cleaned.

Accordingly, there is a need for a customized multi tooth flosser, with an effective floss distribution system, and improved contact between the floss and the inter-proximal tooth surfaces.

SUMMARY OF THE INVENTION

This disclosure is related to an improved custom instant flossing appliance. The custom instant flossing appliance is comprised of a custom fitted mouthpiece formed using any number of a number of processes and materials known in the art. Once the custom-fitted mouthpiece is formed, pairs of holes are located near the gum line at each inter-proximal space between adjacent teeth, one hole on the lingual side (inside) of the appliance and a corresponding hole on the buccal side (outside). A floss distribution system is also provided which dispenses new floss from a reel located between the lingual surfaces of the appliance. This reel is optionally removable, and typically provides a supply of two strands of floss, one for each side of the appliance. Further embodiments include collecting reels located near the rear of the appliance in two positions such that the spent floss can be collected neatly once it has outlived it's usefulness.

Floss supplied from the dispensing reel is fed through a feeder hole near the front of the appliance. It then is threaded through the appliance via the provided inter-proximal holes, such that the floss, starting from the front, is threaded from the buccal side inter-proximal hole to the corresponding lingual side inter-proximal hole, then to the next lingual side inter-proximal hole and the process is repeated until the appliance is fully threaded on each side. The floss can be secured at the back of the appliance on each side by tying the floss to provided buttons, or in more advanced embodiments, attaching it to collecting reels which can wind the floss up once it has been used.

A preferred embodiment is directed to an advanced version of the above mentioned custom instant flossing appliance. In this embodiment, the custom-fitted mouthpiece has two pairs of holes located along the gum line at each inter-proximal space between adjacent teeth, two separated holes on the lingual side (inside) of the appliance and two corresponding holes on the buccal side (outside). In this arrangement, one strand of floss is threaded through one hole on the lingual side of an inter-proximal space across to the diagonally opposed hole on the buccal side, then threaded down to the next buccal hole and the process is repeated. Once one strand of floss is threaded through in this manner, the second strand is threaded through the appliance using the remaining holes in an opposite fashion, creating a x-shaped pattern of two strands of floss at each inter-proximal area. This embodiment of the invention could include the floss distribution system described above.

BRIEF DESCRIPTION OF THE DRAWINGS

Preferred embodiments of the present invention will now be described in greater detail and will be better understood when read in conjunction with the following drawings in which.

DETAILED DESCRIPTION

Persons of ordinary skill in the art will realize that the following disclosure is illustrative only and not in any way limiting. Other embodiments of the invention will readily suggest themselves to such skilled persons having the benefit of this disclosure.

The present invention is designed to fit the entire maxilliary and mandibular arches, while flossing more than one tooth at a time. It is designed in such a way, that when inserted into the individual's mouth, it will cover all upper or lower teeth, and dental floss will pass between the inter-proximal spaces of more than one tooth at the same time (i.e., in a coordinated fashion).

The custom instant flossing appliance is contemplated to be custom-fitted for individual needs, and formed of one contiguous piece of material.

Figure 1:
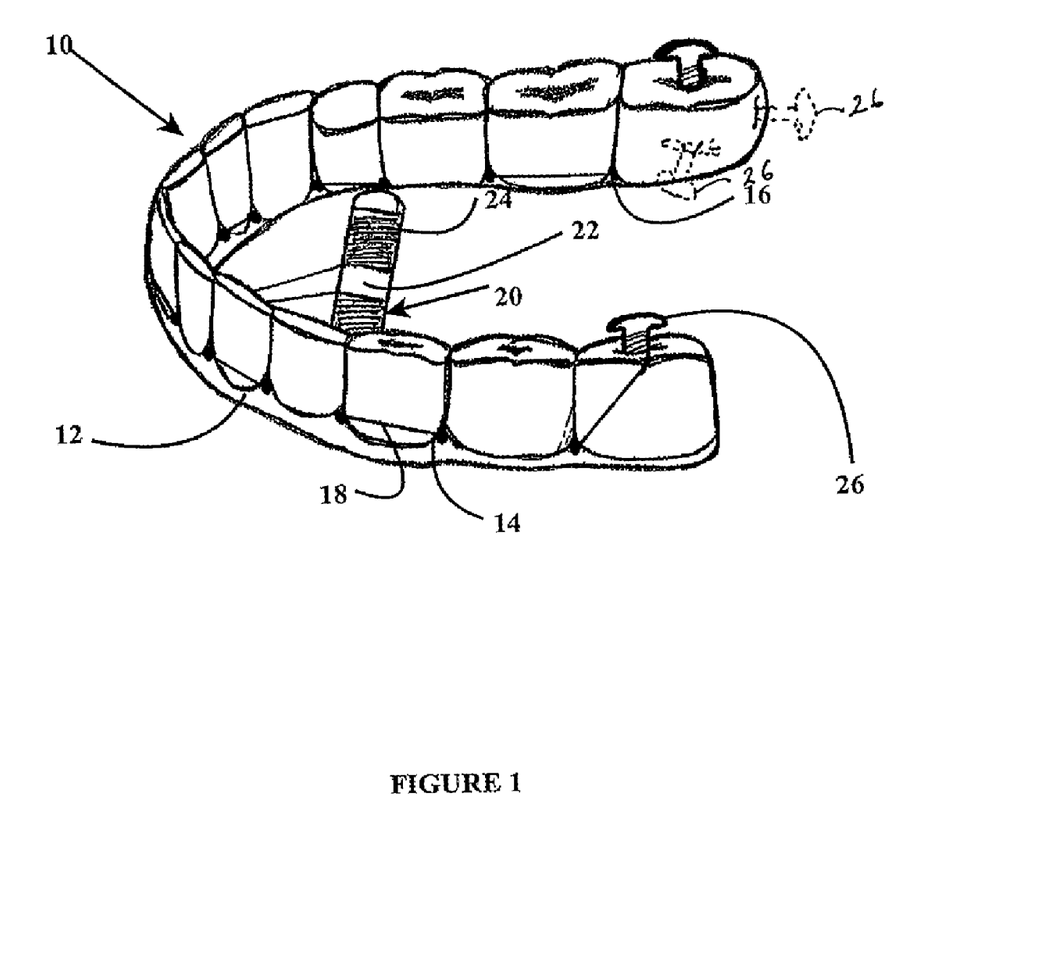
FIG. 1 is a perspective view of the custom instant flossing appliance.
Figure 2:
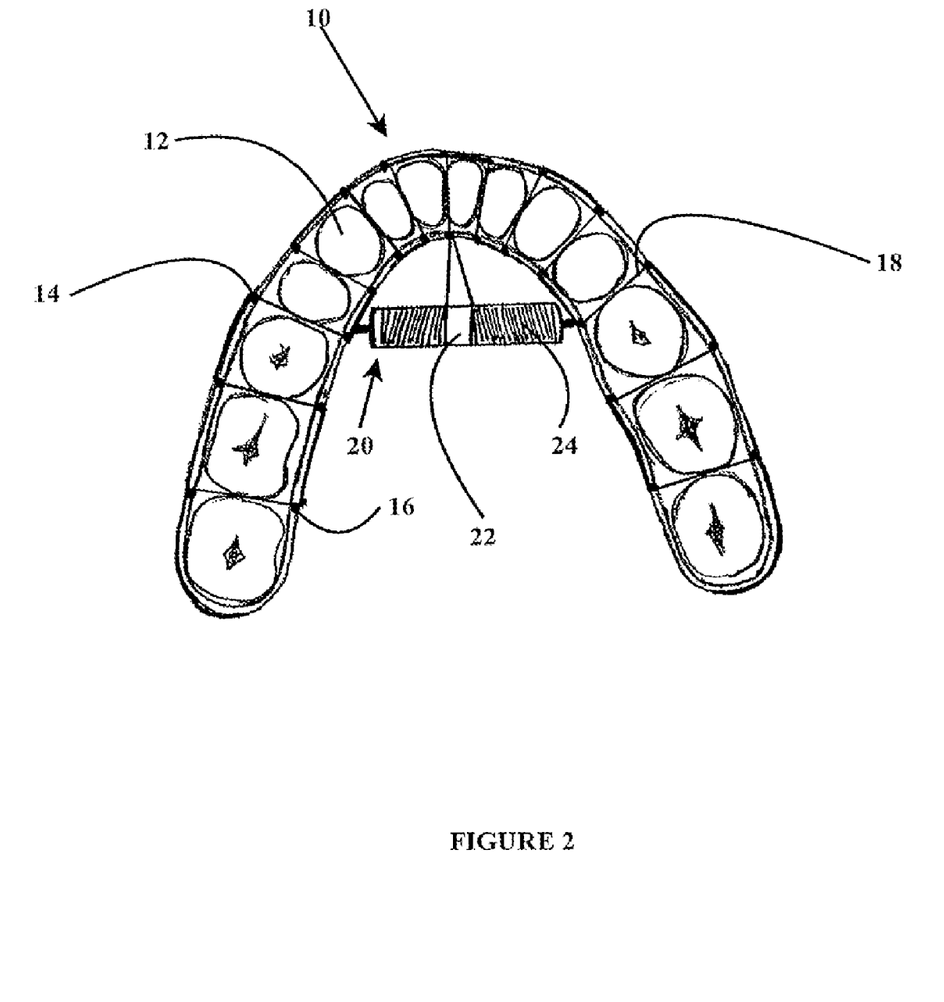
FIG. 2 is a plan view of the custom instant flossing appliance

Referring to FIGS. 1 and 2, one embodiment of the custom instant flossing appliance 10 is illustrated. The appliance 10 includes a custom formed mouthpiece 12 which is fabricated of a material having properties compatible for use in an individual's mouth. It is contemplated that the custom formed mouthpiece 12 can be constructed using any one of a number of orthodontic processes and materials known in the art. The shape and dimensions of the custom formed mouthpiece 12 will vary based on the dimensions of the individual's mouth. Generally, the custom formed mouthpiece 12 will be shaped such that all the teeth from the upper or lower jaw are enclosed on all exposed surfaces, extending slightly past the gum line on the buccal (outside) surface of the teeth. When the custom formed mouthpiece is removed a channel will be provided in which the teeth fit.

In the embodiment illustrated in FIGS. 1 and 2, the custom fitted mouthpiece 12 has a series of holes located near the gum line at each inter-proximal space between adjacent teeth. Inter-proximal holes 14 are located on the buccal side of the appliance and a corresponding set of holes 16 is located on the lingual side of the appliance. Dental floss 18 is threaded through the inter-proximal holes, from the buccal side hole 14 to the lingual side hole 16 (or vice versa). The dental floss 18 is then threaded to the next adjacent hole available and the process is continued. Typically the user would thread each side of the appliance separately starting near the front of the appliance and working towards the back, however different threading arrangements are also contemplated. When completed, the custom fitted mouthpiece 12 will have dental floss 18 threaded between each set of inter-proximal holes such that the floss 18 will insert between adjacent teeth when the custom instant flossing appliance 10 is placed within the mouth.

The inter-proximal holes 14 and 16 on the buccal and lingual sides of the appliance can be fashioned out of any method known in the art. Typically, the holes will be drilled or punched by a skilled lab technician once the custom-fitted mouth piece has been produced and the location for the holes can be properly determined.

In the embodiment illustrated in FIGS. 1 and 2, a floss distribution system 20 is provided that dispenses new dental floss 18 to the custom instant flossing appliance 10. The floss distribution system 20 consists of a spring-loaded reel 22 located between the opposing lingual surfaces of the appliance, which contains a supply of new dental floss 24 for distribution throughout the inter-proximal holes of the appliance. In a typical configuration, the spring-loaded reel 22 will contain two separate supplies of floss 24, one for each side of the custom instant flossing appliance 10. The spring-loaded reel 22 is contemplated to be removable, however it could also be a permanent fixture on the appliance 10.

Dental floss 18 is supplied from the spring-loaded reel 22 through a pair of feeder holes (not shown) in the front of the appliance. Typically, the feeder holes will be the inter-proximal holes located on the lingual side between the front two teeth. The dental floss 18 is then threaded through the appliance 10 in the above mentioned fashion, from the next adjacent buccal side hole 14 to the opposite lingual side inter-proximal hole 16 such that when the appliance 10 is placed in the user's mouth, the dental floss 18 slides into the inter-proximal spaces between the teeth. The dental floss 18 is secured to end means 26 located near the back of appliance 10. Several possible locations for end means 26 are shown. It is contemplated that the end means 26 could be simple posts whereby the dental floss 18 is secured, or additionally the end means 26 could be collecting reels which can wind up the used floss for eventual disposal.

Figure 3:
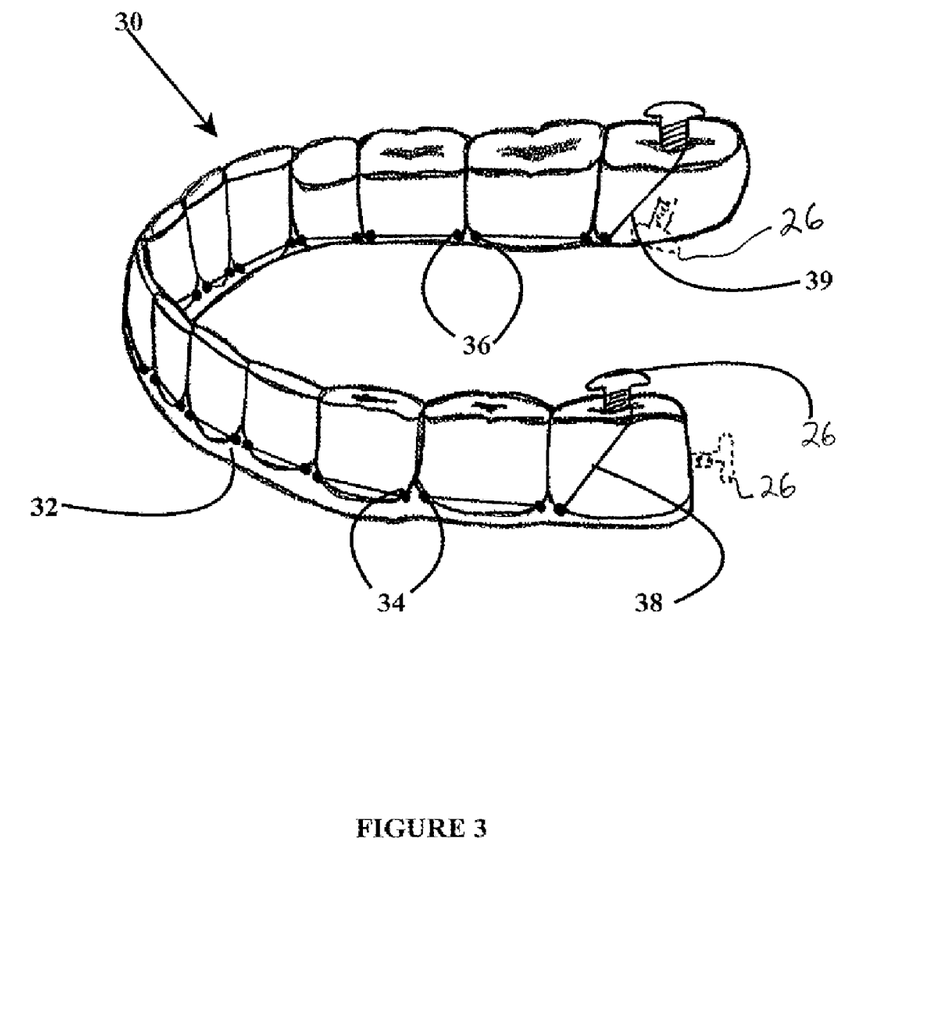
FIG. 3 is a perspective view of the improved custom instant flossing appliance with the cross-flossing configuration.
Figure 4:
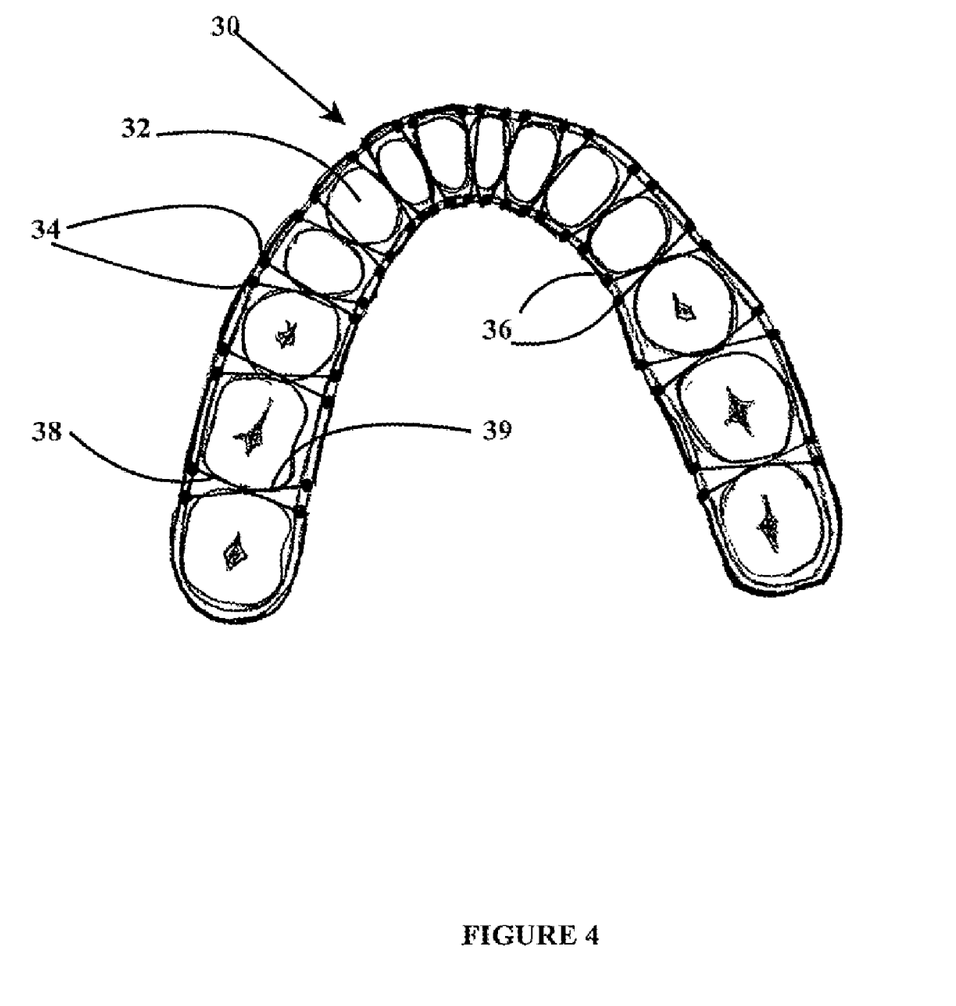
FIG. 4 is a plan view of the improved custom instant flossing appliance with the cross-flossing configuration.
Figure 7:
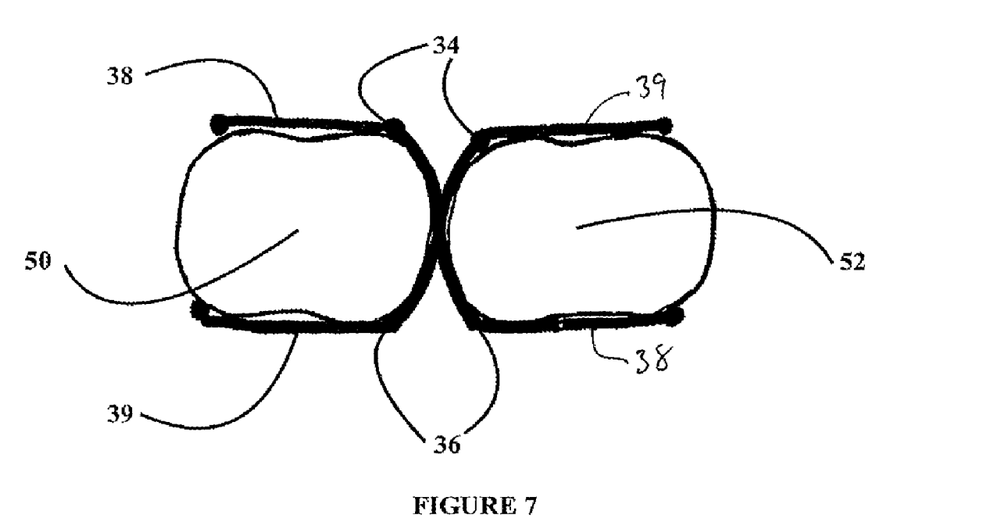
FIG. 7 is a plan view of the inter-proximal space between two molars in the improved custom instant flossing appliance, demonstrating the x-shaped floss pattern.

Referring now to FIGS. 3 and 4, a modified custom instant flossing appliance 30 is illustrated. In this embodiment, custom-fitted mouthpiece 32 is constructed using any one of a number of orthodontic processes known in the art, as described above. Once the mouthpiece 32 has been produced pairs of buccal 34 and lingual 36 inter-proximal holes are located near the gum line at each inter-proximal space between adjacent teeth. The pairs of buccal holes 34 correspond with the lingual holes 36 such that when a first strand 38 of dental floss is threaded from one buccal hole 34 to the diagonally opposed lingual hole 36 and a second strand of floss 39 is threaded from the other lingual hole 36 to the diagonally opposed buccal hole 34, the two strands of floss cross in an x-shaped pattern, as shown in FIGS. 4 and 7. This pattern is continued throughout appliance 30 such that an x-shaped floss pattern is provided at each inter-proximal space between adjacent teeth.

As a result of this x-shaped floss pattern, appliance 30 provides more thorough cleaning of the inter-proximal spaces of adjacent teeth as shown in FIG. 7. When viewed from the tooth's upper surface, one can see that the inter-proximal surface of a tooth is not perfectly flat. The x-shaped floss pattern of appliance 30 follows the contours of the typical inter-proximal tooth surface such that more of the floss maintains contact with the tooth, resulting in improved cleaning. Spacing apart of the corresponding pairs of buccal 34 and lingual 36 holes is selected to provide the desired x-shaped floss pattern such that both strands of floss 38, 39 pass between the inter-proximal spaces of adjacent teeth when appliance 30 is placed in the user's mouth. Location of holes 38, 39 could be carried out by a trained orthodontic laboratory technician once the custom instant mouthpiece 32 is produced from a user's oral impression.

It is also contemplated that cross flossing appliance 30 could include the floss distribution system 20 described above and illustrated in FIGS. 1 and 2.

Figure 5:
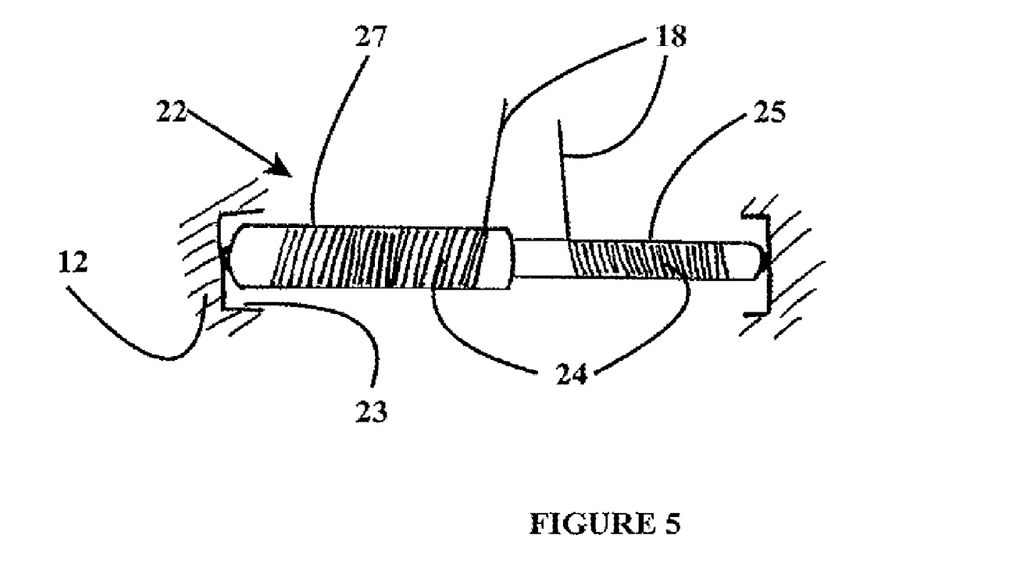
FIG. 5 is a plan view of a spring-loaded reel for the custom instant flossing appliance.
Figure 6:
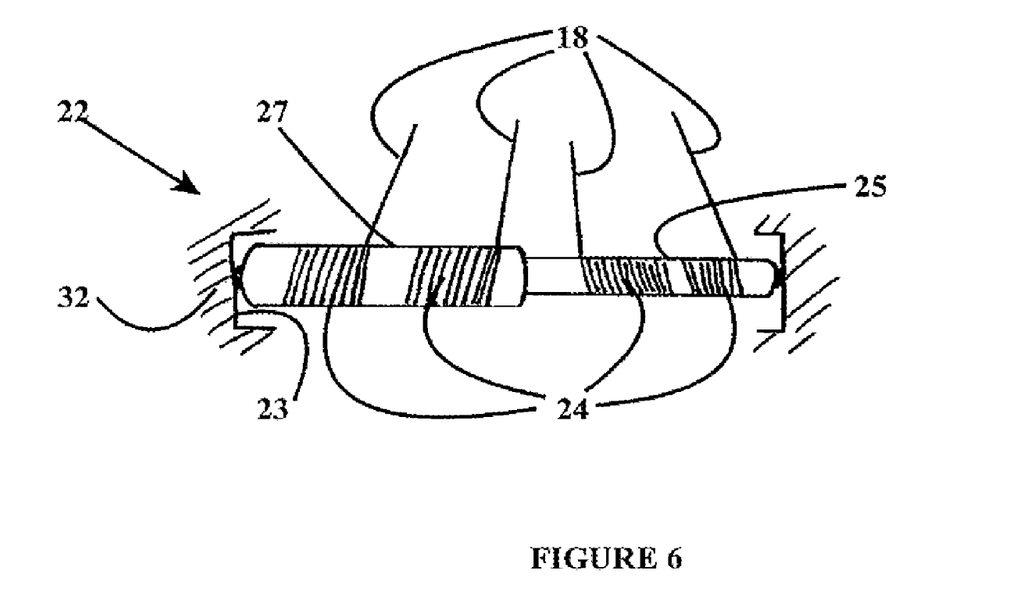
FIG. 6 is a plan view of a spring-loaded reel an improved custom instant flossing appliance.

Referring to FIGS. 5 and 6, two different embodiments of the spring-loaded reel 22 are illustrated. FIG. 5 is a spring loaded reel 22 for the conventional custom instant flossing appliance 20, while FIG. 6 shows a spring loaded reel for appliance 30. Spring-loaded reel 22 is comprised of a large diameter section 27 and a small diameter 25 section. The small diameter section 25 fits telescopically within the large diameter section 27 and the two sections are biased into position via a spring (not shown) located within the interior of the large diameter section 27. The spring-loaded reel 22 fits within reel notches 23 provided on the lingual surfaces of the custom-formed mouthpiece 12, 32. Supplies of new floss 24 are provided on the spring loaded reel, such that dental floss 18 can be unwound and distributed to the flossing appliance 20, 30 in the manner described above.

FIG. 7 illustrates a close up of an inter-proximal space between a first molar 50 and a second molar 52 during use of custom instant cross flossing appliance 30. A first strand of floss 38 is threaded through a buccal hole 34, then threaded to the diagonally opposed lingual hole 36. A second strand of floss 39 is threaded through the remaining lingual hole 36 to the diagonally opposite buccal hole 34, such that the two strands of floss 38, 39 result in an x-shaped pattern which passes through the inter-proximal spaces of the adjacent molars 50, 52. This x-shaped pattern allows greater contract between the floss and the inter-proximal surfaces of the teeth, resulting in improved cleaning.

Figure 8:
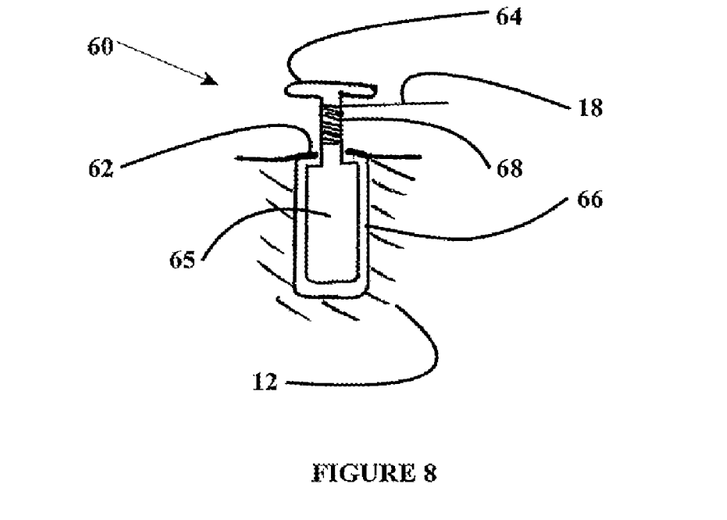
FIG. 8 is a side view of one embodiment of a take-up reel.

FIG. 8 illustrates one embodiment of end means 26 configured as a take-up reel 60. A receiving cavity 66 is formed within the body of the custom formed mouthpiece 132 at a position preferably near the rear of the appliance. The take-up reel 60 is preferably comprised of three elements: A knob 64, a spool section 68 and a cylinder 65. Retaining flanges 62 keep cylinder 65 positioned within cavity 66. When dental floss 18, 38, 39 has reached the end of it's usefulness, it can be wound on take-up reel 60 by turning knob 64, such that the used floss 18 collects on the spool section 68 as new floss is dispensed from reel 22.

Preferably, take up reel 60 will turn in only one direction to prevent the used floss collected on spool 68 from uncoiling. For example, cavity 66 and cylinder 65 can be ratcheted. In this regard, the floss should be held tautly between reel 22 and take-up reel 60 to ensure that the floss enters the inter-proximal spaces between the user's teeth. If reel 22 is removed prior to use of the appliance, the floss can be cut and tied off in front of the pair of feeder holes through which the floss is initially threaded. If reel 22 remains in place during use of the appliance, it can be made lockable so that no floss is released during flossing operations to maintain tautness in the floss.

The above-described embodiments of the present invention are meant to be illustrative of preferred embodiments and are not intended to limit the scope of the present invention. Various modifications, which would be readily apparent to one skilled in the art, are intended to be within the scope of the present invention. The only limitations to the scope of the present invention are set forth in the following claims appended hereto.

The embodiments of the invention in which an exclusive property or privilege is claimed are defined as follows:

1. A custom instant flossing appliance for simultaneously flossing all the user's teeth comprising:
    a custom fitted mouthpiece, comprising:
        at least one pair of inter-proximal holes located at the gum line of at least one inter-proximal area between adjacent teeth, wherein one hole is located on the buccal side of said inter-proximal area and one hole is located on the lingual side of the inter-proximal area;
        two separate strands of floss threaded through said at least one pair of inter-proximal holes of said custom fitted mouthpiece according to the user's tooth pattern;
        a floss distribution system having a removable spring-loaded reel mounted between the adjacent lingual surfaces of said custom fitted mouthpiece wherein said spring-loaded reel contains a supply of said two separate strands of floss, for use in each side of said custom instant flossing appliance;
        feeder holes located at the gum line on the lingual and buccal side of at least one inter-proximal area between adjacent teeth;
        means for securing the ends of said two separate strands of floss;
        wherein said two separate strands of floss are supplied from said removable spring-loaded reel and threaded through said feeder holes and threaded through said at least one pair of inter-proximal holes and secured to said means for securing said two separate strands of floss.

2. The flossing appliance of claim 1 wherein said custom fitted mouthpiece is adapted for use on either the upper or lower set of teeth.

3. The flossing appliance of claim 1 wherein said means for securing said supply of said two separate strands of floss are located in two positions at the rear of said custom instant flossing appliance.

4. The flossing appliance of claim 1 wherein said means for securing said supply of said two separate strands of floss are comprised of:
    reels which can be operated to collect said supply of said two separate strands of floss once it has been used for disposal.

5. An improved custom instant flossing appliance for simultaneously flossing all the user's teeth comprising:
    a custom fitted mouthpiece, comprising:
        at least two pairs of inter-proximal holes located at the gum line of at least one inter-proximal area between adjacent teeth, wherein two holes are located side by side on the buccal side of the inter-proximal area and two holes are located side by side on the lingual side of the inter-proximal area;
        at least two strands of floss wherein one strand of floss is threaded through one hole on each side of said inter-proximal area and another strand of floss is threaded through the remaining hole on each side of said inter-proximal area in an x-shaped pattern;
        means for securing said at least two strands of floss.

6. The custom instant flossing appliance of claim 5 wherein said custom fitted mouthpiece is adapted for use on either the upper or lower set of teeth.

7. The flossing appliance of claim 5 wherein said appliance is further comprised of a floss distribution system for the distribution of new floss and the collection of spent floss.

8. A custom instant flossing appliance for simultaneously flossing all the user's teeth comprising:
    a custom fitted mouthpiece, comprising:
        at least one pair of inter-proximal holes located at the gum line of at least one inter-proximal area between adjacent teeth, wherein one hole is located on the buccal side of said inter-proximal area and one hole is located on the lingual side of the inter-proximal area;
        at least one strand of floss threaded through said at least one pair of inter-proximal holes of said custom fitted mouthpiece according to the user's tooth pattern;
        a floss distribution system having a spring-loaded reel mounted between the adjacent lingual surfaces of said custom fitted mouthpiece wherein said spring-loaded reel contains a supply of said at least one strand of floss;
        feeder holes located in the front portion of said custom fitted mouthpiece;
        means for securing the end of said at least one strand of floss, said means for securing said supply of at least one strand of floss being reels which can be operated to collect said supply of at least one strand of floss once it has been used for disposal;

wherein said at least one strand of floss is supplied from said spring-loaded reel and threaded through said feeder holes and threaded through said at least one pair of inter-proximal holes and secured to said means for securing said at least one strand of floss.

9. The flossing appliance of claim 8 wherein said custom fitted mouthpiece is adapted for use on either the upper or lower set of teeth.

10. The flossing appliance of claim 8 wherein the feeder holes may be located at the gum line on the lingual and buccal side of at least one inter-proximal area between adjacent teeth.

11. The flossing appliance of claim 8 wherein said spring-loaded reel is removable.

12. The flossing appliance of claim 8 wherein said spring-loaded reel contains a supply of two separate strands of floss, for use in each side of said custom instant flossing appliance.

13. The flossing appliance of claim 8 wherein said means for securing said supply of at least one strand of floss are located in two positions at the rear of said custom instant flossing appliance.

* * * * *